(12) United States Patent  
Clark et al.

(10) Patent No.: US 6,592,281 B2
(45) Date of Patent: Jul. 15, 2003

(54) ADHESIVE APPLICATOR TIPS WITH IMPROVED FLOW PROPERTIES

(75) Inventors: Jeffrey G Clark, Raleigh, NC (US); Michael F Brady, Cary, NC (US); Daniel L Hedgpeth, Raleigh, NC (US); William M Cotter, Raleigh, NC (US); Timothy P Hickey, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 10/206,372

(22) Filed: Jul. 29, 2002

(65) Prior Publication Data

US 2002/0176733 A1 Nov. 28, 2002

Related U.S. Application Data

(62) Division of application No. 09/479,059, filed on Jan. 7, 2000, now Pat. No. 6,428,233.

(51) Int. Cl.[7] ............................................. B43M 16/06
(52) U.S. Cl. .................... 401/196; 401/202; 401/265
(58) Field of Search ................................ 401/132, 133, 401/134, 135, 146, 202, 209, 263, 265; 222/81, 89, 90, 91, 190

(56) References Cited

U.S. PATENT DOCUMENTS

| 2,014,149 A | 9/1935 | Stafford |
|---|---|---|
| 2,409,933 A | 10/1946 | Fleisher et al. |
| 2,439,081 A | 4/1948 | Dickey et al. |
| 2,481,803 A | 9/1949 | Weaver |
| 2,768,109 A | 10/1956 | Coover, Jr. |
| 2,784,127 A | 3/1957 | Joyner et al. |
| 3,100,314 A | 8/1963 | Smith |
| 3,178,379 A | 4/1965 | Wicker, Jr. et al. |
| 3,223,083 A | 12/1965 | Cobey |
| 3,260,637 A | 7/1966 | Bramer |
| 3,468,458 A | 9/1969 | Leigh |
| 3,527,841 A | 9/1970 | Wicker, Jr. et al. |
| 3,559,652 A | 2/1971 | Banitt et al. |
| 3,722,599 A | 3/1973 | Robertson et al. |
| 3,728,375 A | 4/1973 | Coover, Jr. et al. |
| 3,759,264 A | 9/1973 | Coover, Jr. et al. |
| 3,770,523 A | 11/1973 | Biswas |
| 3,891,125 A | 6/1975 | Morane et al. |
| 3,940,362 A | 2/1976 | Overhults |
| 3,964,643 A | 6/1976 | Morane et al. |

(List continued on next page.)

FOREIGN PATENT DOCUMENTS

| AU | 36463/89 A | 12/1989 |
|---|---|---|
| DE | 243 183 C | 12/1910 |

(List continued on next page.)

OTHER PUBLICATIONS

Loctite Product No. 11067–2 (Rearview Mirror Adhesive); Jan. 1999.

(List continued on next page.)

Primary Examiner—David J. Walczak
Assistant Examiner—Peter DeVore
(74) Attorney, Agent, or Firm—Oliff & Berridge, PLC (57) ABSTRACT

An article of manufacture for dispensing an adhesive material, such as a synthetic or semi-synthetic polymerizable or cross-linkable monomer material, includes a container body, and a porous applicator tip having a proximal end that is attached to the container body, and a distal end located away from the container body, wherein the adhesive material is located in the container body in a non-contacting relationship with the applicator tip prior to dispensing the material. A flow pattern of the adhesive material within or on the applicator tip is controlled by controlling lengths of flow paths of the material through the applicator tip, forming one or more grooves in the applicator tip, providing a hollow, controlled thickness tip, and/or adding a cover surrounding at least a part but not all of an exposed area of the applicator tip.

35 Claims, 7 Drawing Sheets

U.S. PATENT DOCUMENTS

| | | |
|---|---|---|
| 3,970,505 A | 7/1976 | Hauser et al. |
| 3,995,641 A | 12/1976 | Kronenthal et al. |
| 4,042,442 A | 8/1977 | Dombroski et al. |
| 4,291,131 A | 9/1981 | McIntire et al. |
| 4,297,160 A | 10/1981 | Kusayama et al. |
| 4,340,708 A | 7/1982 | Gruber |
| 4,364,876 A | 12/1982 | Kimura et al. |
| 4,777,230 A | 10/1988 | Kamath |
| 4,801,008 A | 1/1989 | Rich |
| 4,804,691 A | 2/1989 | English et al. |
| 4,875,602 A | 10/1989 | Chickering et al. |
| 5,059,657 A | 10/1991 | Druliner et al. |
| 5,098,297 A | 3/1992 | Chari et al. |
| 5,106,221 A | 4/1992 | Diot et al. |
| 5,216,096 A | 6/1993 | Hattori et al. |
| 5,219,328 A | 6/1993 | Morse et al. |
| 5,230,579 A | 7/1993 | Klawson et al. |
| 5,259,835 A | 11/1993 | Clark et al. |
| 5,262,200 A | 11/1993 | Puder et al. |
| 5,328,687 A | 7/1994 | Leung et al. |
| 5,333,755 A | 8/1994 | Wang et al. |
| 5,514,371 A | 5/1996 | Leung et al. |
| 5,514,372 A | 5/1996 | Leung et al. |
| 5,575,997 A | 11/1996 | Leung et al. |
| 5,582,834 A | 12/1996 | Leung et al. |
| 5,624,669 A | 4/1997 | Leung et al. |
| 5,722,599 A | 3/1998 | Fries |
| 5,816,804 A | 10/1998 | Fischer |
| 5,871,020 A | 2/1999 | DeVone |
| 5,876,139 A | 3/1999 | De Laforcade |
| 5,928,611 A | 7/1999 | Leung |
| 6,161,978 A | 12/2000 | Dovellos |
| 6,322,852 B1 | 11/2001 | Leung |
| 6,352,704 B1 | 3/2002 | Nicholson et al. |

FOREIGN PATENT DOCUMENTS

| | | |
|---|---|---|
| EP | 0 031 893 B1 | 4/1984 |
| EP | 0 170 526 A2 | 2/1986 |
| FR | 2 098 017 A | 3/1972 |
| GB | 467245 A | 6/1937 |
| GB | 2 285 430 A | 7/1995 |
| JP | U 2-135479 | 11/1990 |
| WO | 91/09641 | 7/1991 |
| ZA | 911378 A | 2/1991 |

OTHER PUBLICATIONS

Permatex Product No. ATA–1 (Auto Train Adhesive); Jan. 1999.

Instruction Sheet for Immuno AG product TISSEEL KIT VH, Feb. 1993.

Product Literature for POREX® Plastic Marker Tips, Porex Technologies, 1989.

Product Literature for LABPOR® Porous Products, Porex Technologies, 1989.

Product Literature for LABPOR® Porous Products, Porex Technologies, 1995.

Product Literature for POREX® Porous Plastic Nibs, Porex Technologies, 1995.

ADHESIVE APPLICATOR TIPS WITH IMPROVED FLOW PROPERTIES

This is a Division of application Ser. No. 09/479,059 filed Jan. 7, 2000 now U.S. Pat. No. 6,428,233. The entire disclosure of the prior application(s) is hereby incorporated by reference herein in its entirety.

BACKGROUND OF THE INVENTION

1. Field of the Invention

This invention relates to an improved design for an applicator tip, particularly for use with an applicator that dispenses adhesive material. In particular, the present invention relates to an applicator tip that exhibits an improved flow pattern of the adhesive material in the applicator tip, which allows for more precise placement of the adhesive material and decreased waste of adhesive material.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of adhesive compositions include use as an alternate or an adjunct to surgical sutures and staples in wound closure as well as for covering and protecting surface wounds such as lacerations, abrasions, burns, ulcers such as stomatitis, sores, and other open surface wounds. When an adhesive is applied to surfaces to be joined, it is usually applied in its monomeric form, and the resultant polymerization gives rise to the desired adhesive bond.

However, with the application of adhesive in its monomeric form, due to the rapid polymerization rate of the monomers, it has been challenging to design effective and commercially viable packaging and dispensing systems. Such packaging and dispensing systems must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained.

In order to meet the above requirements, various dispensing and packaging systems for adhesives have been proposed. These systems include large bottles with a single applicator, such as a large single- or multi-use brush; small applicators such as small ampoules containing monomer, for example within an internal frangible vial, that can be expelled through an integral or replaceable applicator; and the like. However, a problem with many of these applicator systems is that the product contains more adhesive material than is necessary for a particular use. Because of the rapid polymerization rate of the monomers, any unused adhesive is generally discarded, because either the remaining monomer undergoes polymerization, or the monomer polymerizes within the applicator to render the applicator unusable.

A disadvantage of some known applicator systems, and particularly applicators containing a frangible vial and a porous applicator tip for expelling the adhesive, is that monomer material may be wasted by filling the pores of the applicator tip in areas other than the areas used to apply the adhesive. Furthermore, some known applicator tips suffer from the problem of the monomer being expelled through the entire surface area of the tip, and even to greater extents in areas other than the area used to apply the monomer to the desired substrate. For example, large amounts of adhesive become expelled from areas around the periphery of the applicator tip, where the applicator tip meets the applicator housing, rather than through the end of the applicator tip, as is often desired. This leads to a further problem of less precise control over the area of application of the monomer to the substrate.

Figure 1:
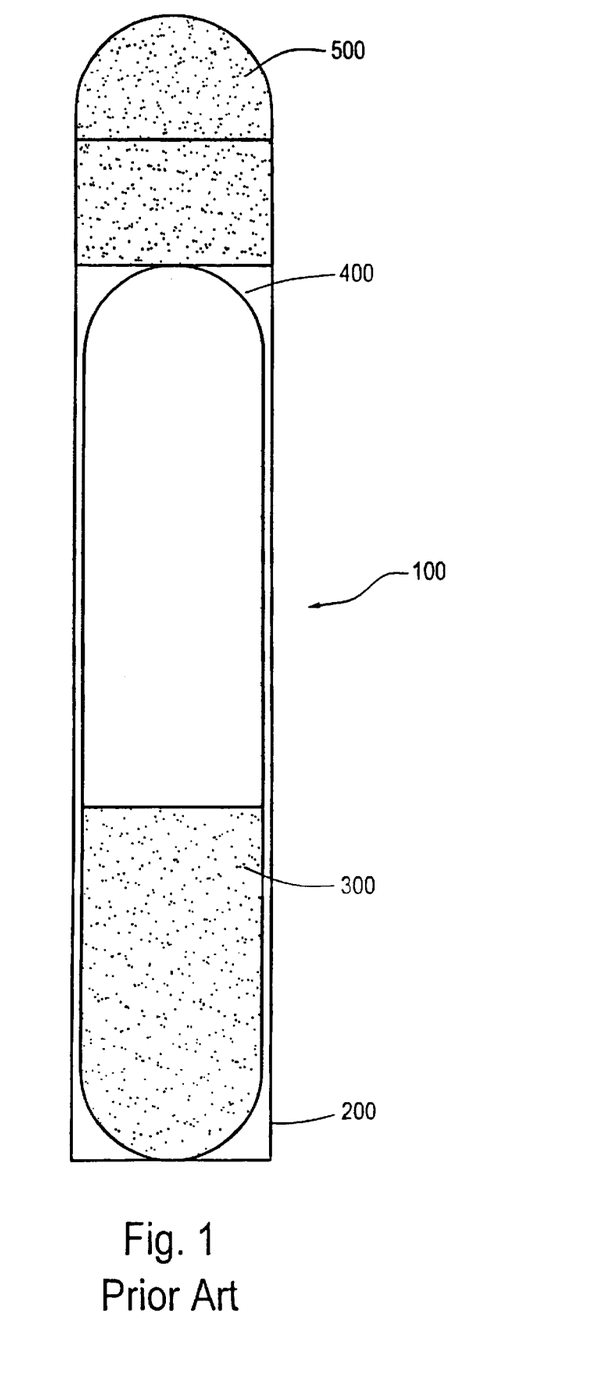
FIG. 1 is a side elevational view of an applicator device according to the prior art.

For example, an effective applicator system is disclosed in U.S. Pat. No. 5,928,611 to Leung. This patent discloses an applicator system generally comprising a tube containing a frangible vial of monomeric adhesive composition. One end of the tube is sealed, and the other end is closed by an applicator tip comprising a solid support having a polymerization or cross-linking accelerator or initiator for the monomeric adhesive disposed thereon or therein. As shown in FIG. 3 of the patent, the applicator tip can be generally dome shaped. An applicator device of U.S. Pat. No. 5,928,611 is shown as FIG. 1 herein. The applicator device 100 comprises a cylindrical applicator container 200 holding polymerizable and/or cross-linkable material 300 enclosed in a frangible vial 400, and an applicator tip 500 containing a polymerization and/or cross-linking initiator.

However, a difficulty encountered with such a dome-shaped applicator tip, as well as with other solid applicator tips, is that the monomeric adhesive material being expelled through the applicator tip tends to follow paths of least resistance within the tip. That is, as the monomeric adhesive is being expelled, it tends to follow the shortest paths through the tip, which tend to be around the periphery of the tip, rather than following the longer path through the full length of the tip to the end of the tip. Because the end of the tip is desired to be used to apply the adhesive, less precise control of placement of the adhesive is obtained because adhesive becomes expelled through the entire surface of the tip. This also tends to result in waste of adhesive material, because all of the adhesive does not exit from the tip at the same location.

Applicator devices commercially used for Loctite Product No. 11067-2 and Permatex Product No. ATA-1 contain crushable glass ampoules within flexible applicators. However, the compositions within the crushable ampoules are, in both products, adhesive activators, not the adhesive composition itself. In both of these products, the adhesive is contained in a separate dispenser. The dispenser system used for these products is physically similar to that shown in FIG. 1, except that the applicator tip is rectangular in shape, rather than dome-shaped, and the applicator tip does not contain a polymerization and/or cross-linking initiator for an adhesive material contained in the frangible vial. In this product also, the above-described problems of wasted material (here, initiator) and less precision in application are also present.

Accordingly, a need exists in the art for improved applicator tip designs, which will allow more precise placement of the adhesive material. A need also exists in the art for a means to decrease waste of monomeric adhesive material, by ensuring that the adhesive material either exits at the desired location of the applicator tip, or flows to such a desired location on the tip.

SUMMARY OF THE INVENTION

The present invention addresses the above needs by providing applicator tips that possess increased precision in control of placement of the adhesive composition, and a decrease in waste of adhesive. The applicator tips of the present invention provide either more uniform or preferentially controlled paths of resistance within the applicator tip, or provide means for channeling adhesive to an application zone and away from other surface areas of the applicator tip.

A benefit provided by the present invention is thus the ability to apply adhesive material in precise patterns, such as in thin lines. The present invention also allows tailoring of the application pattern based on alternative designs of the applicator tip, thus allowing flexibility in application of, for example, from thin lines to thicker lines. The present invention also decreases waste of adhesive material, by allowing effective use of a greater portion of the volume of adhesive material contained within the applicator. In embodiments, it also improves the utilization of polymerization and/or cross-linking initiator and/or rate modifiers present in the tip.

The present invention provides an article of manufacture for dispensing adhesive material, comprising a container body, and a porous applicator tip having a proximal end that is inserted into or attached to the container body, and a distal end located away from the container body, wherein the adhesive material is located in the container body in a non-contacting relationship with the applicator tip prior to dispensing the adhesive material.

In embodiments of the present invention, a flow path length ratio A/B is less than 1.5, wherein B represents a length of a shortest flow path of adhesive material through the material of the applicator tip to an external surface of the applicator tip adjacent the container body, and A represents a length of a shortest flow path of the adhesive material through the material of the applicator tip to an external surface of a predetermined application subportion such as the distal end of the applicator tip. In embodiments, the applicator tip comprises one or more grooves that channel adhesive exiting the applicator tip from peripheral portions of the applicator tip to the distal end of the applicator tip. In embodiments, the applicator comprises a protective cover surrounding at least a part but not all of an area of the applicator tip extending out of the container body. In embodiments, the applicator tip is a hollow porous applicator tip having a proximal end that is inserted into or attached to the container body, and a distal end located away from the container body.

DETAILED DESCRIPTION OF EMBODIMENTS

The present invention provides improved applicator tips and applicator devices that provide significant improvement in the application and use of adhesive material. Such applicator tips can be used, for example, in combination with the adhesive compositions and packaging and dispensing systems set forth in U.S. Pat. No. 5,928,611, the entire disclosure of which is incorporated herein by reference. Of course, other adhesive compositions, compatible with the applicators of the present invention, can also be used.

In embodiments of the present invention, an improved applicator tip is provided wherein the shape and/or construction of the applicator tip is selected so as to control the flow pattern of the adhesive through and/or on the applicator tip. For example, the shape of the applicator tip can be selected so as to control the flow paths of the adhesive material, or the surface of the applicator tip can be configured to channel adhesive material exiting the applicator tip to a predetermined location, preferably the location used to apply the adhesive.

Figure 2:
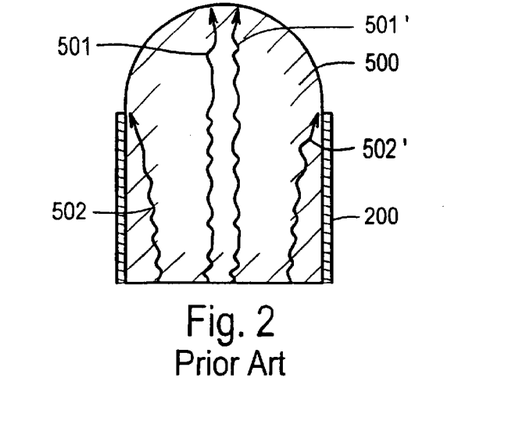
FIG. 2 is a cross-sectional view of an applicator tip according to the prior art.

For example, in the prior art, the lengths of the flow paths of the adhesive are generally longer from the inside of the applicator to the end of the tip than they are from the inside of the applicator to the periphery or edge surfaces of the applicator tip adjacent the end of the container body. This is shown, for example, in FIG. 2. FIG. 2 is an enlarged scale, cross-sectional view of the prior art applicator tip 500. FIG. 2 shows simplified schematics of the flow paths of adhesive material through the applicator tip 500 to areas outside of the container body 200. In FIG. 2, the flow paths 501,501' through the applicator tip to the end of the tip are longer than, for example, the flow paths 502,502' to the periphery or external surface of the applicator tip. In the prior art applicator tip, the flow path length 501 is about 11 mm, and the flow path length 502 is about 7 mm, giving a ratio of 1.57. Thus, because the flow paths 502,502' are shorter than the flow paths 501,501', more of the adhesive composition tends to follow these paths.

One means for controlling and improving flow properties according to the present invention is to select the overall shape of the applicator tip. Accordingly, in an embodiment of the present invention, the shape of the applicator tip is selected to provide flow paths of more uniform length, or even of reversed proportions, from the inside of the applicator to the periphery of the applicator tip. Examples of such applicator tips according to the present invention are shown in cross-section in FIGS. 3a–3d.

Figure 3A:
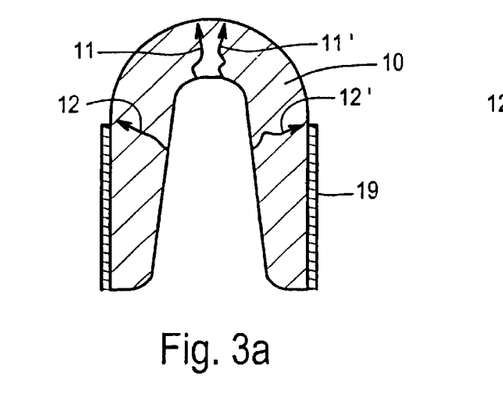
FIGS. 3a–3d are cross-sectional views of applicator tips according to the present invention.

FIG. 3a is a cross-sectional view of an applicator tip 10 according to the present invention. FIG. 3a shows simplified schematics of the flow paths of adhesive material through the applicator tip 10 to areas outside of the container body 19. In FIG. 3a, the lengths of the flow paths 11,11' through the material of the applicator tip to an external surface of the end of the tip are more closely equal to, for example, those of the flow paths 12,12' through the material of the applicator tip to an external surface of the applicator tip adjacent the container body. That is, as compared to the corresponding flow paths in the applicator tip of FIG. 2, the flow paths to the end of the tip are shorter in FIG. 3a than in FIG. 2. Thus, because the lengths of the flow paths 11,11' are more equal to those of the flow paths 12,12', there is more uniform flow of the adhesive through the applicator tip, and the adhesive composition tends to flow or express more uniformly through the applicator tip.

Figure 3B:
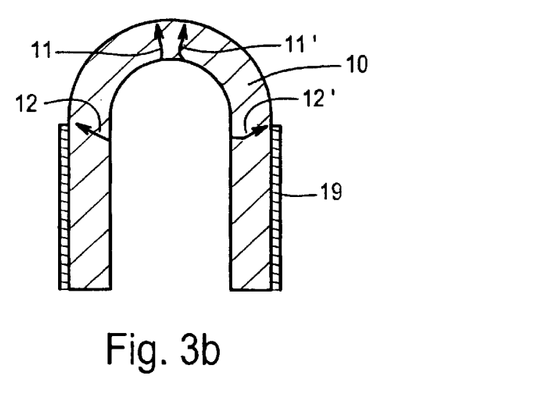

In embodiments of the present invention, the applicator tip 10 can assume different shapes, as desired. For example, the end of the applicator tip located nearest the frangible vial, i.e., located within the applicator body 19, can have different shapes as shown in non-limiting fashion in FIGS. 3a–3d. For example, the end of the applicator tip can be curved or otherwise designed to equilibrate the flow path lengths. As shown in FIG. 3b, the lengths of the flow paths 11,11' through the material of the applicator tip to an external surface of the end of the tip are substantially equal to, for example, those of the flow paths 12,12' to an external surface of the applicator tip adjacent the container body. This thus provides a more uniform expression of the adhesive material through the entire surface of the applicator tip.

Reversed flow profiles, such as where more adhesive flows through the distal end of the applicator tip than through peripheral or side portions of the applicator tip, can also be provided. For example, in the applicator tip shown in FIG. 3d, the flow paths through the material of the applicator tip at the distal end are shorter than flow paths to the remaining surface of the applicator tip.

Alternatively, or in addition, the end of the applicator tip can be shaped so as to accommodate the frangible vial. In these embodiments, the curvature or shape of the end of the applicator tip located nearest the frangible vial can be designed to more closely match the shape of the frangible vial. However, it is preferred that a tight fit between the frangible vial and the internal surface of the applicator tip is not made, so that there is sufficient room for adhesive material to exit the frangible vial and enter and pass through the applicator tip. That is, for example, it is preferred that the frangible vial does not enter the tip, which can be accomplished, for example, by providing a frangible vial that has a diameter greater than the internal diameter of the curved portion of the applicator tip.

In embodiments of the present invention, it is preferred that the walls of the applicator tip are of substantially uniform thickness as shown in FIG. 3b. Because the flow pattern of the adhesive through the applicator tip is related to the length of the flow path through the applicator tip, providing substantially equal flow distances helps to provide equal flow throughout the applicator tip. Of course, the applicator tip walls can be made thinner in desired areas, such as toward the end of the applicator tip, if desired. This would tend to increase flow of the adhesive through the thinner portions.

Figure 3C:
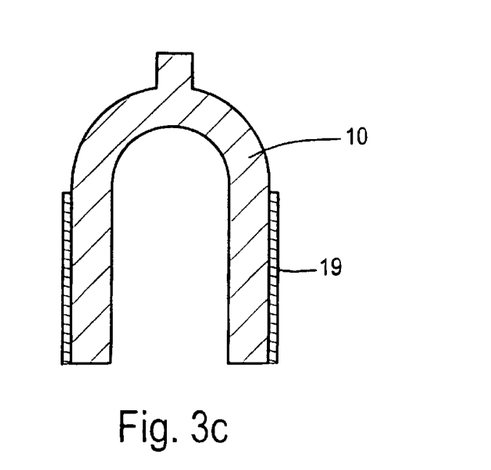
Figure 3D:
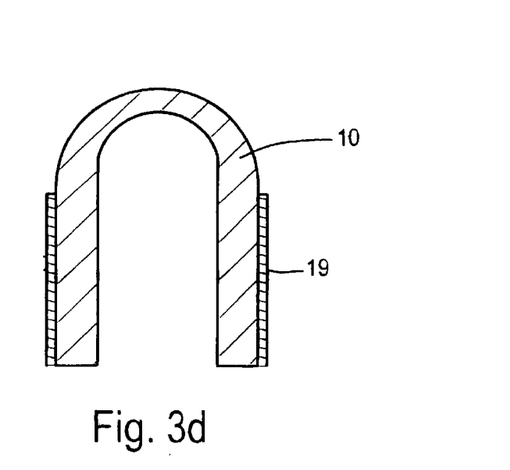

Still further, in embodiments of the present invention, the end of the applicator tip located furthest from the frangible vial, i.e., located outside of the applicator, can have different shapes as shown, for example, in FIGS. 3a and 3c. For example, the end of the applicator tip can have a smooth curvature, as in FIG. 3a, for application of the adhesive material. Alternatively, or in addition, the end of the applicator tip can be configured so as to provide, for example, more precise application of the adhesive material. For example, as in FIG. 3c, the applicator tip can have an extension portion thereon, which draws the adhesive material to a more defined application area. This extension can have any shape and dimension and can, for example, be tubular, conical, rounded, or the like.

Likewise, the overall shape of the applicator tip can be any of various shapes. For example, suitable shapes of the applicator tip are shown in FIGS. 3a–3d as being a dome-shape. However, the present invention is not limited to such shapes. Rather, any suitable size and shape applicator tip can be used. Generally, the dimensional characteristics are limited only by the intended use of the applicator, and practicality considerations. Suitable shapes include, but are not limited to, conical, cylindrical, chisel or polygonal shapes. Furthermore, the desired shapes can be either solid (i.e., having a substantially flat (or planar) bottom end, as shown in FIG. 2), curved (i.e., having a curved bottom end, as shown in FIG. 3a), or hollow (i.e., having a substantially hollow bottom end, as shown in FIGS. 3b and 3c). Of course, other geometries can be used, as desired. The length and size of the tip can be varied depending on various application parameters. The tip may be detachable from the applicator body, or may be an integral part of the applicator.

Figure 5A:
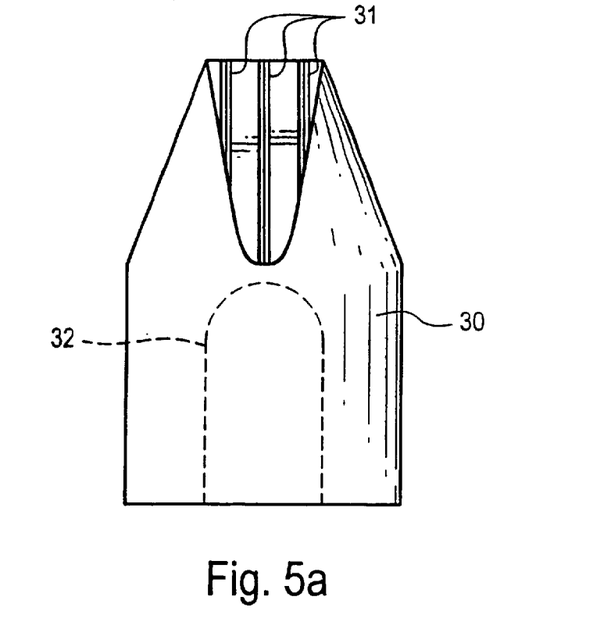
FIGS. 5a–5d are elevational views of applicator tips according to the present invention.
Figure 5B:
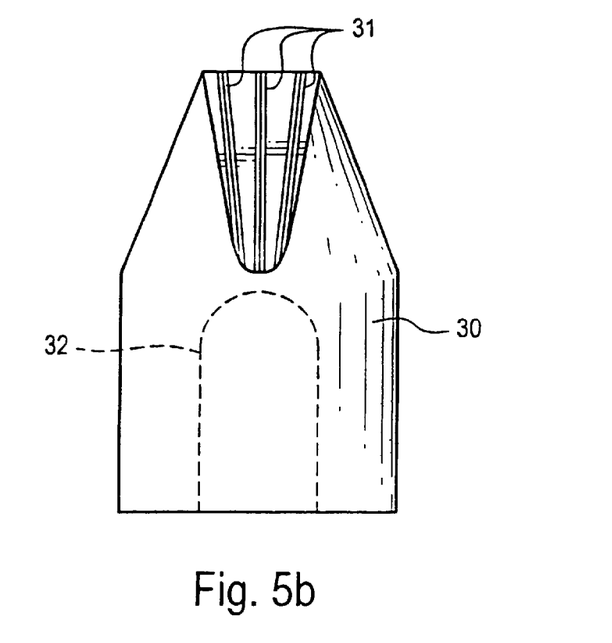
Figure 5C:
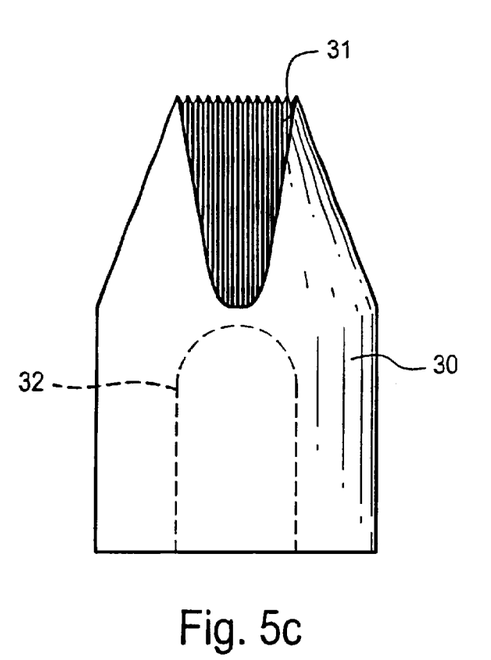
Figure 5D:
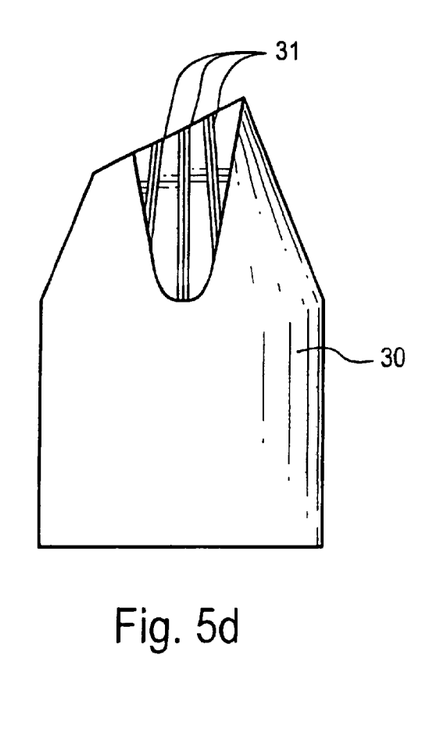

In the case of using chisel tips, and even other shaped tips, the distal end of the applicator tip can come to a sharp point (such as a chisel shape being formed by two intersecting planar portions). Alternatively, the distal end of the applicator tip can be rounded over, or can have a flattened shape, such as by not having the planes intersect at the distal end. Still further, as shown in FIG. 5d, the applicator tip can have other configurations, such as being formed similar to a marker tip to permit more comfortable and natural use of the applicator.

Because it is desired in embodiments of the present invention to control and equalize adhesive flow through the applicator tip, it is preferred in embodiments that the proximal end of the applicator tip, i.e., the end nearest the frangible vial or adhesive material, be shaped so as to help achieve such controlled flow. Thus, for example, the proximal end of the applicator tip may be curved, cut-out or hollowed to at least some extent. As used herein, "hollow" is meant to refer to a shape of the applicator tip where a distinct lumen is present in the applicator tip, as opposed to a porous tip where numerous pores define open space within the applicator tip. Thus a porous tip may or may not also be hollow.

In embodiments, the shape of the applicator tip can be formed by any suitable means or manufacturing process. For example, the hollow shaped applicator tips can be formed by molding the applicator tip material into the desired hollow or other shape, or a solid material can be shaped and/or hollowed, for example, by drilling, filing, boring, cutting, gauging, or the like.

In these embodiments of the present invention, the shape of the applicator tip is selected so as to control the length of the adhesive material flow paths within the applicator tip. By so controlling the lengths of the flow paths, the distribution of adhesive exiting the applicator tip can be made more uniform, or can establish a specific desired distribution. Thus, for example, whereas the flow rate of adhesive in the prior art may have been higher at the periphery or side surfaces of the applicator tip than at the distal end of the applicator tip, the applicator tips of the present invention can provide a more uniform, preferably substantially uniform, flow pattern or expression throughout the exposed surface of the applicator tip. In other embodiments, the shape can be selected such that the flow path length within the applicator tip is less in the direction to the end or another desired portion of the applicator tip than it is to other areas of the applicator tip, for example the peripheral or side areas. That is, in these embodiments, a higher distribution of adhesive is expressed in the application area than in the periphery or side portions of the applicator tip. Such distribution helps to prevent waste of adhesive material, and provides for improved precision of application of the adhesive.

According to embodiments of the present invention, a more uniform profile of adhesive expression is provided in the applicator tip. This can be obtained, for example, by providing an applicator tip wherein the lengths of the shortest flow paths of the adhesive through the material of the applicator tip are substantially equal over the exposed portion of the applicator tip. For example, the lengths of the flow paths can be approximated and measured by measuring a shortest distance of travel of adhesive through the material of the applicator tip to an outer surface of the applicator tip.

Thus, for example with reference to FIGS. 3a and 3b, the shortest flow paths to an external surface of the applicator tip adjacent the applicator body are represented by lines 12,12'. Likewise, the shortest flow paths to the distal end of the applicator tip are represented by lines 11,11'. In measuring the lengths of the flow paths, the distance within the open or hollowed-out area of the applicator tip is not included in the length of the flow path, because this distance is open space that does not impede adhesive flow. If the length of the shortest flow path through the material of the applicator tip to an external surface of the applicator tip adjacent the applicator body is denoted B, and the length of the shortest flow path through the material of the applicator tip to an external surface of the distal end of the applicator tip is denoted A, then the value A/B can be used to represent a flow path length ratio. In embodiments of the present invention, it is preferred that the flow path length ratio be less than 1.5, preferably less than 1.3, more preferably about 1 or less than 1. In embodiments, this ratio is preferably about 1, indicating that the flow paths in the applicator tip are substantially uniform, and that there are no significantly shorter flow paths. In other embodiments, this ratio can be adjusted so as to be less than 1, such as less than or equal to about 0.9, 0.8 or 0.5 or less, indicating that the monomeric adhesive material encounters shorter flow paths through the material of the applicator tip to the point of application of the adhesive, such as the distal end of the applicator tip, than to other areas of the applicator tip.

A further benefit of embodiments of the present invention is that the total pore volume of the applicator tip can be decreased. As a result, less of the adhesive material gets trapped in the pores of the applicator tip, resulting in less waste of material.

In embodiments of the present invention, an alternative or additional approach to controlling and improving flow properties is to alter the surface of the applicator tip, for example to channel adhesive material exiting the applicator tip to a common location, preferably the location used to apply the adhesive. One means to accomplish this objective is to form channels in the surface of the applicator tip. These channels will cause adhesive material exiting the applicator tip to flow on the surface of the tip to the desired area of application. Thus, for example, where a dome-shaped or cone-shaped or chisel-shaped applicator tip or the like is used, channels can be formed in the surface of the tip to channel adhesive material exiting on the periphery to travel towards the end of the applicator tip.

Figure 4:
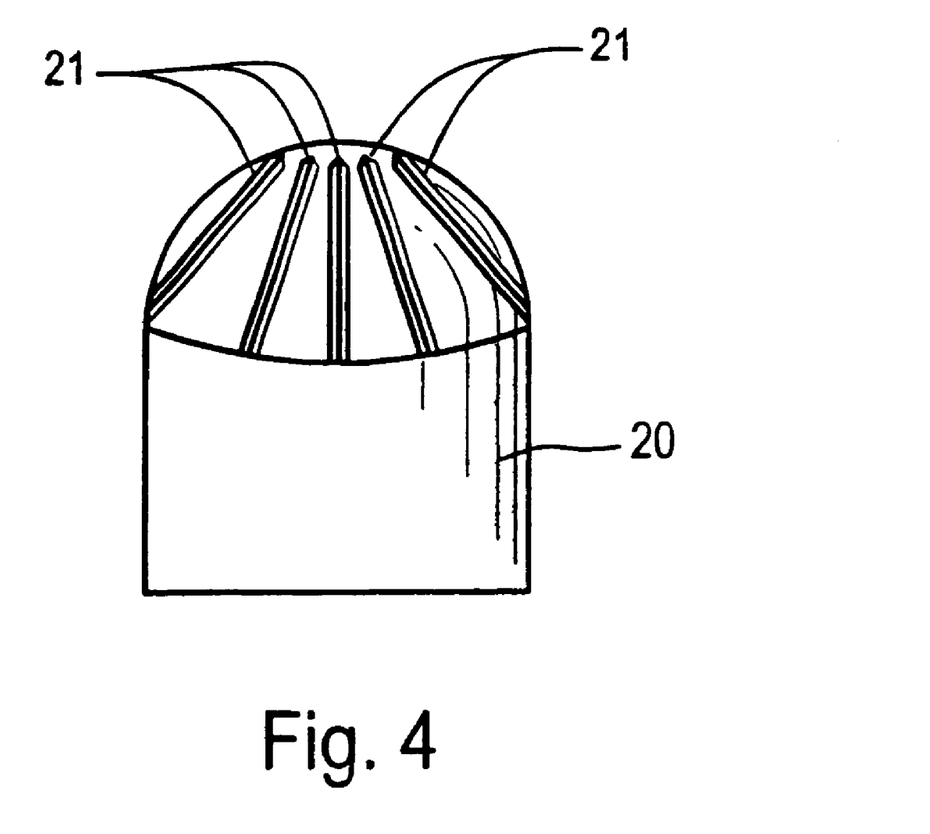
FIG. 4 is an elevational view of an applicator tip according to the present invention.

FIG. 4 shown an exemplary applicator tip according to this embodiment of the invention. As shown in FIG. 4, the applicator tip 20 has formed in the surface thereof multiple channels or grooves, shown as v-shaped grooves 21, which converge toward the end of the applicator tip. Of course, such grooves need not be v-shaped, but can assume any desired shape so long as the function of channeling adhesive material to the application area is achieved. For example, the grooves or channels can be v-shaped, u-shaped, square, semi-circular, semi-oval, or the like. In addition, the grooves or channels can be formed such that they are exposed on the surface, or they can be formed to be located beneath the surface of the applicator tip.

Furthermore, in this embodiment of the present invention, the applicator tip need not be dome-shaped, as shown in FIG. 4. Rather, any suitable applicator tip shape can be utilized. For example, a particularly suitable applicator tip shape is a chisel-shape. As shown in FIGS. 5a–5b, the applicator tip can be shaped, for example, as a generally dome shape with two opposing substantially planar faces formed to define a chisel tip at the end of the applicator tip. That is, the chisel tip is formed by two intersecting planes in the applicator tip.

When such a chisel shape is used for the applicator tip, the intersecting planes forming the tip can be formed at any desired angle, based for example on the desired use of the applicator. For example, the angle of intersection forming the chisel tip can, in embodiments, be anywhere from 5 to 170°. Preferably, the angle of intersection is between about 20 and about 90°, more preferably between about 40 and about 70°. Of course, values outside of these ranges can be used, in embodiments, as desired.

The tip 30 can also have formed in the surface thereof multiple channels or grooves, as described above and shown as v-shaped grooves 31, which converge at the chisel tip end of the applicator tip. Of course, such grooves need not be v-shaped, but can assume any desired shape as described above so long as the function of channeling adhesive material to the application area is achieved. FIGS. 5a–5c also show a central interior portion of the applicator tip 30 hollowed out, as shown by dashed lines 32. As described above, such design is optional, and can be present or not, as desired. Thus, as shown in FIG. 5d, the central portion can be solid.

As also shown in FIGS. 5a–5b, the grooves formed in the surface of the applicator tip can be parallel to each other, or can be offset at a desired angle. For example, as shown in FIG. 5a, the grooves 31 can be generally parallel to each other, so that adhesive material travelling through the bulk applicator tip is channeled to the chisel end of the applicator tip. However, as shown in FIG. 5b, the grooves can be offset (i.e., non-parallel) by a desired amount. This may be desirable, for example, where it is known that a larger amount of adhesive material passes through the central portion of the applicator tip as compared to the outer portions of the applicator tip. By making the grooves 31 non-parallel, the adhesive material flowing through the central portion of the applicator tip can be dispersed along the width of the chisel tip. This aids in providing a more uniform coating of adhesive material on the desired surface.

In embodiments of the present invention where the grooves are made nonparallel on the face of the applicator tip, it is suitable to offset the grooves at any desired angle. For example, adjacent lines can be offset at an angle of, for example, from about 1 to about 15°. Preferably, the adjacent grooves are offset at an angle of from about 2 to about 10°, more preferably from about 3 to about 7°.

Furthermore, this embodiment of the present invention is not limited to the chisel shape shown in FIGS. 5a–5b. Rather, any suitable shape can be used to achieve particular results in use of the applicator. For example, where chisel shapes are used, the shape, width, and slope of the chisel shape can be adjusted to provide different results. For example, a wide chisel tip can be provided where a wide area of application is desired, while a narrow chisel tip can be provided where a thin or narrow area of application is desired. Alternatiuvely, the tip can be provided in other shapes, such as conical shapes, pyramidal shapes, and the like, where the end of the application tip either comes to a point, is rounded over, or is flattened.

Although FIGS. 5a, 5b and 5d show the applicator tip as containing only three grooves on the visible face of the applicator tip, the invention is not so limited. Rather, one or more grooves can be formed on each face of the applicator tip. Such grooves can be either separated by a planar (or curved) surface, as in FIGS. 5a, 5b and 5d, or the grooves can be located continuous and adjacent to each other, as shown in FIG. 5c. Furthermore, although the grooves are shown as being placed only on the planar faces of the chisel-shaped tip, the present invention is not limited to such embodiments. Rather, if desired, the grooves can additionally, or alternatively, be placed on non-planar portions of the applicator tip. Such placement could further channel the exiting adhesive composition to the desired point of application.

In these embodiments of the present invention, the shape of the applicator tip and the number and placement of grooves on the surface of the applicator tip are also selected so as to alter the effective distribution of adhesive material on the surface of the applicator tip. By providing grooves on the surface of the applicator tip, the effects of gravity, surface tension and capillary action act to draw the exiting adhesive material from the non-application areas of the application tip to the application area of the applicator tip. Thus, for example, whereas the adhesive distribution on the surface of the applicator tip in the prior art may have been higher at the periphery of the applicator tip, the applicator tips of the present invention can provide a higher quantity of adhesive material at the application area, and lesser quantities of material on the remaining surface of the applicator tip. Accordingly, the travel of the adhesive material is effectively channeled or "focused" to the application area. Such channeling helps to prevent waste of adhesive material, and provides for improved precision of application of the adhesive material.

In embodiments of the present invention, the flow pattern of adhesive material from the applicator tip can be altered by blocking flow from desired portions of the applicator tip. Thus, for example, if it is desired that adhesive material exits only through the end of the applicator tip, and not through peripheral portions, such flow pattern can be accomplished by altering the design of the applicator tip to block flow through such undesired areas. This can be accomplished, for example, by altering the physical structure of surface areas of the applicator tip, such as by filling the pores of such areas with a material that will prevent flow through those areas, or by covering the areas with a separate material to prevent flow.

As used herein, the term "cover" is used to refer to any suitable means for preventing adhesive material from exiting through desired portions of the applicator tip. Thus, as will be described below, a "cover" includes physically separate components that are placed on or attached to the applicator tip to block adhesive flow, can be a coating or layer applied to the surface of the applicator tip to block adhesive flow, or can be the result of a method of altering at least the surface layer of the applicator tip so as to likewise block adhesive flow.

Figure 6A:
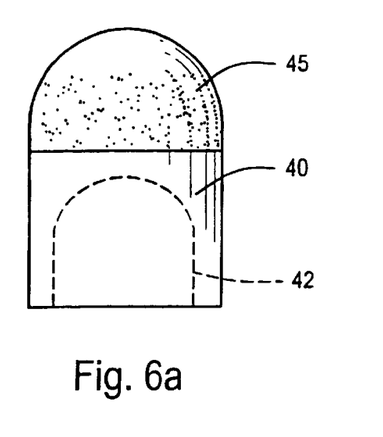
FIGS. 6a–6d are elevational views of applicator tips according to the present invention.
Figure 6B:
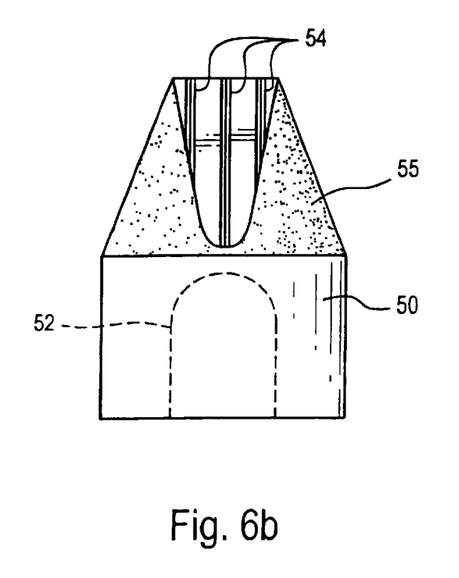

For example, FIGS. 6a–6d show exemplary embodiments of the present invention where the flow pattern is adjusted by blocking the exit of adhesive material from desired areas of the applicator tip. In FIG. 6a and FIG. 6b, the applicator tips 40,50 are shown as being treated in portions to prevent adhesive from exiting the applicator tip in the treated areas. FIG. 6a represents a hollow dome-shaped applicator tip, whereas FIG. 6b represents a chisel-shaped applicator tip having grooves 54 formed in the flat surfaces thereof. In each of these embodiments, the areas 45,55 (shown in the Figures using stipling) of the applicator tip are treated or coated so as to block exit of the adhesive material, such that the material does not exit to the surface of the applicator tip. In these embodiments, the adhesive material will thus be forced to proceed through the applicator tip and exit only in the desired areas.

In these embodiments, any suitable treatment or coating material may be used to treat or coat the otherwise exposed surfaces of the applicator tip to prevent adhesive material from exiting in those areas. For example, the applicator tip can be coated by a cured form of the adhesive material, other cured or curable polymeric materials, materials that provide barrier properties upon setting, or the like. Likewise, any suitable material may be coated upon the desired surface of the applicator tip, which provides the desired blocking characteristics to the applicator tip. For example, suitable solid, semi-solid, or liquid particles can be directly applied to the applicator tip surface, or can be dispersed in a suitable coating material (such as a solvent, dispersant or the like) and coated onto the applicator tip. For example, acceptable results can be obtained by dissolving polymeric materials, such as butyrate, in a suitable solvent, such as acetone, and coating the resultant solution onto the desired portions of the applicator tip. As a further example of the above, suitable materials such as paints, sealants, or the like can be applied onto the desired portions of the applicator tip to provide the adhesive blocking property.

Alternatively or in addition, the treatment can include any suitable method that alters the properties of the surface of the applicator tip. For example, heating, melt smearing, ultrasonic welding, spray coating or the like can be used at the desired portions of the tip so as to close the pores in that area. Likewise, a suitable material can be applied to the applicator tip to close the pores. For example, applying a suitable solvent, such as acetone or the like, can close the pores of the applicator tip. Preferably, such treatment affects only the surface of the applicator tip, or only to a small depth of the applicator tip, so as not to plug the applicator tip or otherwise render it inoperable.

Figure 6C:
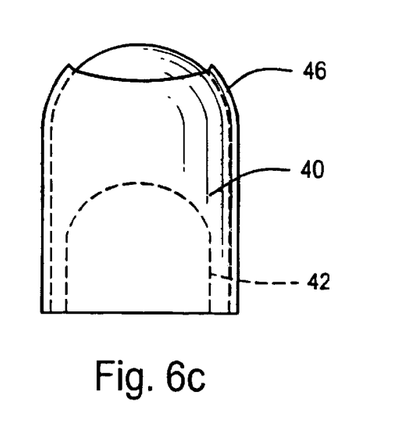
Figure 6D:
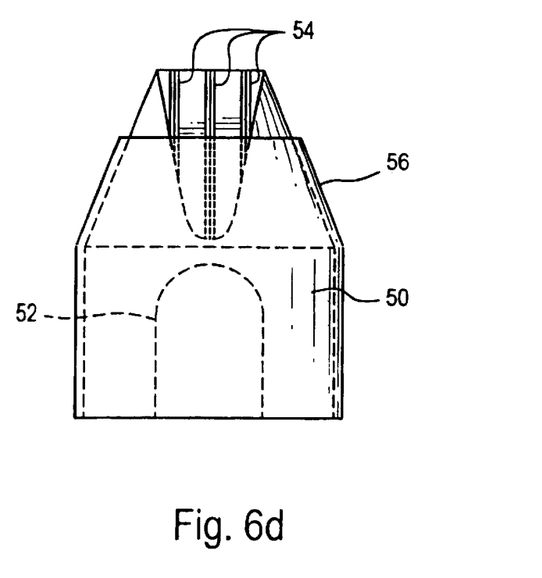

In alternative embodiments, shown in FIGS. 6c and 6d, the applicator tips 40,50 are shown as being covered in portions by a separate component that prevents adhesive from exiting the applicator tip in the covered areas. FIG. 6c represents a hollow dome-shaped applicator tip, whereas FIG. 6d represents a chisel-shaped applicator tip having grooves 54 formed in the flat surfaces thereof. In each of these embodiments, areas of the applicator tip are covered with a separate component or cover 46,56 to block exit of the adhesive material, such that any adhesive material that exits to the surface of the applicator tip is not exposed to the environment. In these embodiments, the bulk of the adhesive material will thus be forced to proceed through the applicator tip and exit only in the desired areas.

In these embodiments, the cover 46,56 is a separate component, which can be applied to the applicator tip as part of the manufacturing process, or can be applied to the applicator tip by the user prior to use. The cover 46,56 can be attached to the applicator tip by any suitable means.

As used herein, the terms "attach" or "attached" as referring to the applicator tip means operably connecting the applicator tip to the applicator body, or parts thereof, directly or through other components. Thus, for example, the applicator tip can be attached to the applicator body in any suitable way, including but not limited to mechanical arrangements such as luer locks, threads or locking rings, pressure and/or friction fitting, adhesive or chemical arrangements such as adhesive or chemical bonding, heat-shrink attachment, ultrasonic welding, and the like.

For example, the cover can be adherently bonded to the applicator tip, can be attached to the applicator tip by heat-shrinking the cover onto the applicator tip, can be screwed onto the applicator tip by suitable threads or locking rings (not shown) or can be held to the applicator tip by pressure and/or friction. Adherent or heat-shrink attachment may be preferred in embodiments where the cover is not to be interchangeable, or where the cover is attached during the manufacturing process. However, screw, locking or friction/pressure attachment may be preferred in embodiments where interchangeability is desired, such as where different sizes or types of covers are available. Such interchangeable tips can be used, for example, to provide different degrees of coverage of the applicator tip or to alter the profile of application of the adhesive material.

In these embodiments, any suitable material may be used to form the cover, which in turn covers the otherwise exposed surfaces of the applicator tip to prevent adhesive material from exiting in those areas. For example, the covers can be made from natural materials such as cellulose, cardboard, metal, ceramic, plastics such as butyrate or high density polyethylene, polypropylene, polyester, or the like. Alternatively, the cover can be formed from the tip material itself, such as from the surface layer of the tip material, such as by the above-described processes.

In FIGS. 6a–6d, the applicator tip is shown as having a hollow central interior portion of the applicator tip 40,50, as shown by dashed lines 42,52. As described above, however, such design is optional, and can be present or not, as desired.

According to the present invention, the applicator can be attached to a suitable applicator body, such as a tube, in any suitable way. For example, the applicator tip can be attached to an end of the applicator body by annealing, bonding or form-fitting the applicator tip into or onto an opening in the applicator body. In embodiments of the present invention, the applicator tip can be attached to the applicator body using a luer lock configuration. Luer lock configurations provide a benefit of being able to change the applicator system, such as changing the design of the applicator tip, without the resulting need to redesign the entire product configuration. That is, by providing a Luer lock mechanism on the applicator body, any of various applicator tips can subsequently be applied to the applicator body.

According to this aspect of the present invention, the luer lock connector can also provide the desired effect of channeling the adhesive material toward a desired external surface application subportion of the applicator tip, such as the distal end of the applicator tip. This can be accomplished because a portion of the applicator tip can be hollowed out to accept the luer lock connector. Thus, as the adhesive material flows through the luer lock connector, it flows through further toward the application subportion before actually entering the material of the applicator tip. Accordingly, the luer lock can provide the double effect of providing a means of attaching the applicator tip to the applicator body, and providing shorter flow path lengths of the adhesive through the material of the applicator tip.

Figure 7A:
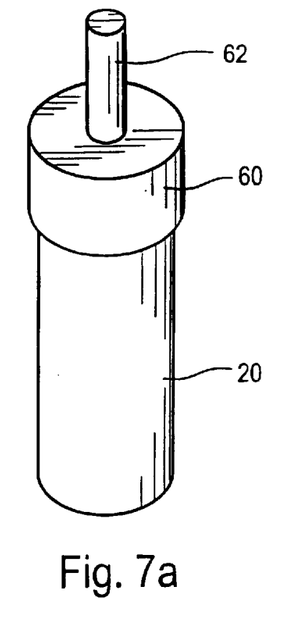
FIGS. 7a–7c are elevational views of a luer lock connection for attaching an applicator tip to an applicator body.
Figure 7B:
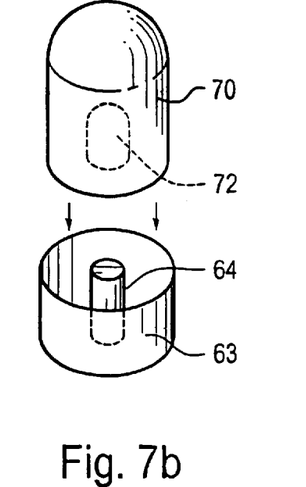
Figure 7C:
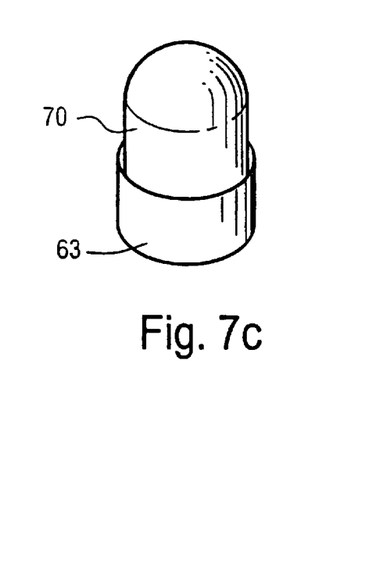

When used, the luer lock connection can be made in any desired configuration. Suitable constructions of the luer lock mechanism are shown in non-limiting fashion in FIGS. 7a–c. FIG. 7a shows an exemplary applicator body 20 having attached to one end a cap 60 having a male luer lock connector 62. The cap 60 can be made of any suitable material, such as the same materials that are used to form the applicator body 20. A corresponding female luer lock connector 64 is supported in a tip retainer and support member 63, as shown in FIG. 7b. The tip retainer and support member or platform 63 can be formed in any configuration as desired, but are depicted as having an open area into which the applicator tip can be placed. Such a platform could be formed, for example, by injection molding the platform around an applicator tip, by forming the applicator tip around a preformed platform, or by attaching a preformed applicator tip to a preformed platform. Preferably, as shown in FIG. 7b, the applicator tip 70 includes a hollow area or void 72, suitable for receiving the female luer lock connector 64 when the tip retainer and support member 63 is mated with the applicator tip. Once mated, the components form a unitary component, as shown in FIG. 7c.

Figure 8:
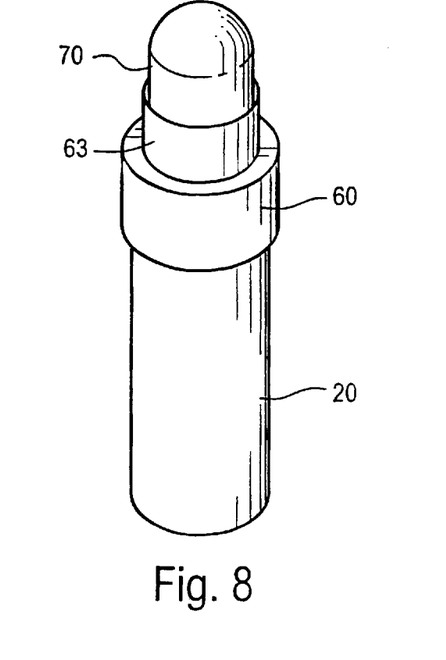
FIG. 8 is an elevational view of an assembled applicator device using the luer lock system of FIGS. 7a–7c.

The applicator tip bearing the luer lock connector can then be attached to the applicator body bearing a corresponding luer lock connector, to form a complete applicator device, as shown in FIG. 8. Of course, although this embodiment has been described herein as the applicator body having a male luer lock connector and the applicator tip as having a female luer lock connector, the invention is not so limited. Rather, these connectors can be reversed, as desired.

According to the present invention, the applicator can include any suitable adhesive material. The adhesive material can include monomeric (including prepolymeric) materials, polymeric materials, or mixtures thereof. The monomer (including prepolymeric) adhesive composition may include one or more polymerizable monomers. Preferred adhesive compositions for use in applicators of the present invention are useful as tissue adhesives, sealants for preventing bleeding or for covering open wounds, and in other biomedical applications. They find uses in, for example, apposing surgically incised or traumatically lacerated tissues; retarding blood flow from wounds; dressing burns; dressing skin or other superficial or surface wounds such as compromised skin or other tissue (such as abrasions, chaffed or raw skin, minor cuts and scrapes, sores and/or ulcers such as stomatitis); protecting intact skin; and aiding repair and regrowth of living tissue. Adhesive compositions of the present invention are also useful in industrial and home applications, for example in bonding rubbers, plastics, wood, composites, fabrics, and other natural and synthetic materials.

Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Particularly preferred adhesive materials are 1,1-disubstituted ethylene monomers including, but not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$–C$_4$ alkyl group. Examples of monomers within the scope of formula (I) include α-cyanoacrylates, such as ethyl, butyl, and/or 2-octyl cyanoacrylate, vinylidene cyanides, $C_1$–$C_4$ alkyl homologues of vinylidene cyanides, dialkyl methylene malonates, acylacrylonitriles, vinyl sulfinates and vinyl sulfonates of the formula $CH_2=CX'Y'$ wherein X' is —$SO_2R'$ or —$SO_3R'$ and Y' is —CN, COOR', —$COCH_3$, —$SO_2R'$ or —$SO_3R'$, and R' is H or hydrocarbyl.

Furthermore, the adhesive composition contained in the applicator can further include various additives as are known in the art, including but not limited to flavorants, preservatives, plasticizing agents, stabilizing agents, formaldehyde concentration reducing agents, pH modifiers, thickening agents, cross-linking agents, fibrous reinforcement agents, colorants, and the like.

Suitable compositions, methods of making such compositions, and methods for incorporating such compositions into a dispenser device are described, for example, in U.S. Pat. Nos. 5,928,611 to Leung; U.S. Pat. Nos. 5,328,687, 5,514,371, 5,514,372, 5,575,997, 5,582,834 and 5,624,669, all to Leung et al; U.S. Pat. No. 5,259,835 to Clark et al.; U.S. Pat. No. 3,527,841 to Wicker et al.; U.S. Pat. No. 3,722,599 to Robertson et al.; U.S. Pat. No. 3,995,641 to Kronenthal et al.; and U.S. Pat. No. 3,940,362 to Overhults; and U.S. patent application Ser. Nos. 08/266,647, 08/714,288, 09/099,457, 09/430,177, and (100497.02 filed Oct. 29, 1999), the entire disclosures of which are incorporated herein by reference.

According to the present invention, the applicator tip may, but need not, include a polymerization and/or cross-linking initiator and/or rate modifier, such as an accelerator or inhibitor, for a polymerizable monomer adhesive material contained in the applicator. Suitable polymerization and/or cross-linking initiators and rate modifiers, and methods for applying them to the applicator tip, are described in, for example, U.S. Pat. No. 5,928,611 and U.S. patent application Ser. No. 09/430,177, filed Oct. 29, 1999, Ser. Nos. 09/430,176, 09/430,289, 09/430,290, and 09/430,180 filed Oct. 29, 1999; Ser. No. 09/343,914 filed Jun. 30, 1999; Ser. No. 09/385,030 filed Aug. 30, 1999; and Ser. No. 09/176,889 filed Oct. 22, 1998, the entire disclosures of which are incorporated herein by reference. Preferred initiators for some medical uses include benzalkonium chloride, and for some industrial uses include dimethyl toluidine.

The polymerization and/or cross-linking initiator and/or rate modifier may be applied to the applicator tip by any suitable means, including, but not limited to, spraying, dipping, injecting, or brushing the applicator tip with a liquid medium containing the polymerization and/or cross-linking material. It is preferably applied to the tip by dipping or injecting. For example, it may be applied to the tip by pumping of the liquid medium, for example, through a syringe, onto the distal end of the applicator tip.

The polymerization and/or cross-linking initiator and/or rate modifier may be applied to porous applicator tips by using a vacuum or pressure process. In each process, a solution or suspension of the polymerization and/or cross-linking initiator and/or rate modifier is introduced into a vacuum or pressure chamber. The applicator tips, either individually or preferably in batches, are placed into the solution or suspension in the pressure vessel in a manner such that the applicator tips preferably do not float to the top of the solution or suspension. For example, the applicator tips can be placed in the solution or suspension in a wire basket or other suitable container, which would hold the applicator tips under the solution or suspension, or a wire mesh or other suitable retainer could be placed over the applicator tips to dunk or sink them into the solution or suspension. Once the applicator tips are in the solution or suspension, the vessel can be sealed and an appropriate vacuum or pressure applied.

Application of the vacuum or pressure results in air that is trapped in the applicator tips being degassed, or forced out of the applicator tips, and being replaced by the solution or suspension. This replacement of air by the solution or suspension thereby loads the material onto or into the applicator tips. The end of the degassing phase can be observed by the absence of newly formed air bubbles. After a desired treatment time, the vacuum or pressure in the vessel can be released, and the treated applicator tips can be removed.

In exemplary embodiments, preparing an applicator for dispensing polymerizable monomeric compositions includes applying a material to a suitable applicator tip, such as a porous polyethylene, foam or fibrous tip, which is attached to an applicator body, such as a butyrate applicator tube or other suitable holder.

When the applicator is intended to contain an amount of polymerizable monomeric composition, the applicator body or tube may comprise a conduit or reservoir for the polymerizable monomeric composition. In this embodiment, the applicator tip may be operably connected to the conduit or reservoir, such as by being fitted on an open end of the conduit, so that fluid flowing through the conduit also flows through the applicator tip.

In addition to the polymerization and/or cross-linking initiator and/or rate modifier, the applicator tip can also include various other materials that may or may not act as a polymerization initiator and/or rate modifier. For example, the applicator tip can include a flavorant, such that it imparts a flavor to the adhesive material when the adhesive material is applied to a surface. Incorporation of a flavorant is particularly preferred, for example, when the cyanoacrylate adhesive material is to be applied to oral surfaces, such as to treat ulcers such as stomatitis or cold sores. Similarly, the applicator tip can include a bioactive material, which may or may not also be a polymerization and/or cross-linking initiator and/or rate modifier. Examples of suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof.

The applicator tip may be composed of any of a variety of materials including polymerized materials such as plastics, foams, rubber, thermoset resins, films, fibers, or membranes. Where foams are used in the applicator tip, the foam can be either an open-celled form, a closed-cell foam, or a mixture thereof. Any suitable foam material can be used and suitable foams include, for example, thermoplastic polyurethane foam, preferably a soft, absorbent thermoplastic polyurethane foam.

In embodiments, the applicator tip may be made from polyurethane, polyesters, polyolefins such as polyethylene, or polyamides. In embodiments, the applicator may be made from polyethylene, such as that sold by Porex Technologies Corp. (Fairburn, Ga.) under the trademark LabPor®. In embodiments, the applicator tip can also be made from fibers, either natural or synthetic, such as cotton, rayons, nylons, and mixtures thereof. Additionally, the applicator tip may be composed of materials such as metal, glass, paper, ceramics, and the like. The applicator tip material may be porous, absorbent, or adsorbent in nature to enhance and facilitate loading of a material on or in the applicator tip. For example, the porous applicator tip may be composed of a material having random pores, capillaries, a honeycomb material, a material having a woven pattern, etc. The degree of porosity will depend on the materials being used, and can be determined by one of ordinary skill in the art without undue experimentation. Porosity is the open volume within the pores of an applicator tip divided by the total volume of the applicator tip.

In embodiments, the applicator tip may be porous and have an average pore size of about 1 μm to about 500 μm. Generally, according to the present invention, an applicator tip having an average pore size of about 1–100 μm such as 10–30 is used with a polymerizable material having a viscosity of about 1–30 cP, preferably about 2–18 cP, and more preferably 5–7 cP at 25° C. An applicator tip having an average pore size of from about 1 μm to about 100 μm is preferably used with a polymerizable material having a viscosity of about 10–30 cP. When the polymerizable and/or cross-linkable material has a viscosity higher than 7 cP, the average pore size of the applicator tip is generally increased. For example, an applicator tip having an average pore size of about 40–300 μm such as 60–125 μm is preferably used with a polymerizable material having a viscosity of about 30–500 cP, preferably about 35–350 cP, and more preferably about 50–200 or 60–140 cP at 25° C. In embodiments, an applicator tip has a pore volume of less than or equal to 80 percent, preferably between 20–60 percent.

In embodiments of the present invention, the adhesive composition has a viscosity of about 1–5000 centipoise, preferably 1–600 centipoise, more preferably 1–100 or 2–50 centipoise such as 2–18, 2–10 or 5–7 centipoise, or 30–500 such as 50–100 or 100–200 centipoise at 25° C. The viscosity can be selected according to the proposed use—e.g., 1–100 centipoise for certain uses and 100–200 centipoise for other uses. Additionally, the composition may be a gel, e.g., 50,000–500,000 centipoise at 25° C. Such gels are particularly advantageous in embodiments of the present invention, because the gels are more easily expelled through the applicator due to the decreased resistance to travel through the applicator tip provided by the present invention. The viscosity of the adhesive composition can be measured with a Brookfield Viscometer. Additionally, in embodiments where a sterilization treatment is applied, the viscosity of the composition should preferably be maintained or increased by a controlled and acceptable amount after sterilization.

The applicator tip according to the present invention, where it connects to the applicator tube, may have an elongated tubular portion, out of which the mixed polymerizing and/or cross-linking material is expelled. A portion of the applicator tip that is immediately downstream of the applicator tube is advantageously porous in order to avoid a sharp pressure drop and ensure a constant mixed ratio profile. The structure can preferably trap fragments of any barriers or materials used to separate one or more components within the applicator container so that they will not clog the device or contact the patient or surface onto which the adhesive is being applied.

When using a porous applicator tip to apply the adhesive composition, the composition preferably is not expressed directly through the applicator tip in a continuous motion. According to embodiments of the present invention, the adhesive composition is (1) expressed to the end or part way to the end of the applicator tip, (2) the pressure is released to draw the composition back into the applicator, and (3) the composition is then subsequently expressed through the applicator tip in a continuous motion. This is called a suck-back method of applying the adhesive composition of the present invention. When used with a tip that bears an initiator, this method lets the adhesive composition polymerize better than if it had been expressed directly through the tip.

According to the present invention, the applicator can be manufactured in any of various ways, generally known in the art. For example, an applicator tube can be sealed at one end, and a frangible vial containing the monomeric adhesive material can be placed in the applicator tube. The remaining open end of the applicator tube can then be sealed by filling it with the applicator tip, which can be bonded or form-fit into the opening in the applicator tube. Such applicator tip can be previously prepared to incorporate the polymerization initiator or rate modifier, or the polymerization initiator or rate modifier can be applied to the applicator tip subsequent to placing the applicator tip on the applicator. Furthermore, if desired, a second applicator tip, of the same or different design or configuration as the first applicator tip, can be affixed at the opposite end of the applicator tube rather than sealing the applicator tube. Such second applicator tip can have the same of different constructions as those described above.

However, the present invention further provides an alternative means for forming the applicator assembly. According to embodiments of the present invention, the applicator tip can be first applied to an open end of the applicator body, and the polymerization initiator or rate modifier can be applied to the applicator tip through the length of the applicator body. Once the initiator is applied, the frangible vial can be inserted into the applicator body, and then the remaining open end of the applicator body can be sealed.

According to this embodiment of the present invention, the applicator tip is first applied to an open end of the applicator body. The applicator tip can be applied to the applicator body by any suitable method, as described above. Next, the polymerization initiator or rate modifier is applied to the applicator tip. The polymerization initiator or rate modifier can be applied, for example, by dispensing the material onto the back (inside or proximal) end of the applicator tip, for example, by using a standard dispensing nozzle or injection syringe.

Once the polymerization initiator or rate modifier has been applied to the applicator tip, the frangible vial containing the monomeric adhesive material can be inserted into the applicator tube. In this manner, the frangible vial can rest up against the back end of the applicator tip.

Next, the remaining open end of the applicator body is sealed. The sealing can be affected by any suitable means known in the art. For example, the applicator tube can be sealed by heat, the open end can be covered, for example by a cap, or the like. Where a separate cap is used to seal the applicator body, it is preferred that the cap is bonded to the applicator body, for example by ultrasonic welding, chemical bonding, physical bonding (such as adhesive), or the like.

Once the applicator assembly is prepared, the assembly (or individual components thereof) can be sterilized according to known practices. Compatibility of the adhesive composition and the applicator with one or more sterilization procedures is preferred in embodiments of the present invention because many uses of the adhesive compositions, such as many surgical and other medical applications, require sterilized products. In preferred embodiments, there is substantially no initiation of polymerization of monomeric liquid adhesive compositions that affects the utility of the monomer or monomers caused by the sterilization process.

Sterilization of the monomer composition and/or its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation. In embodiments where a composition is to be used for medical applications, the sterilized composition must show low levels of toxicity to living tissue during its useful life.

While the invention has been described with reference to preferred embodiments, the invention is not limited to the specific examples given, and other embodiments and modifications can be made by those skilled in the art without departing from the spirit and scope of the invention.

What is claimed is:

1. An article of manufacture for dispensing an adhesive material, comprising:
    a container body,
    a porous applicator tip having a proximal end that is attached to said container body, and a distal end located away from said container body,
    an adhesive material located in said container body in a non-contacting relationship with said applicator tip prior to dispensing said material, wherein said adhesive material is a polymerizable or cross-linkable monomer material, and
    a cover surrounding at least a part but not all of an area of said applicator tip extending out of said container body, and preventing said adhesive material from exiting said applicator tip at said covered area, while permitting said adhesive material to exit said applicator tip at an uncovered area.

2. The article of claim 1, wherein said cover is attached to said applicator tip.

3. The article of claim 1, wherein said cover is attached to said applicator tip by an adhesive material.

4. The article of claim 1, wherein said cover is attached to said applicator tip by chemical bonding.

5. The article of claim 1, wherein said cover is attached to said applicator tip by ultrasonic welding.

6. The article of claim 1, wherein said cover is attached to said applicator tip by heat-shrinking the cover onto said applicator tip.

7. The article of claim 1, wherein said cover is attached to said applicator tip by pressure or friction fitting.

8. The article of claim 1, wherein said cover is attached to said container body.

9. The article of claim 1, wherein said cover is a coating of material applied to said part of said applicator tip.

10. The article of claim 9, wherein said material is a cured or curable polymer material.

11. The article of claim 1, wherein said cover is an in situ polymerized coating.

12. The article of claim 1, wherein said cover is formed by altering properties of a surface layer of the applicator tip.

13. The article of claim 12, wherein said cover is formed by at least one of heating, melt smearing and ultrasonic welding said part of said applicator tip.

14. The article of claim 1, wherein said cover snugly matches contours of said applicator tip.

15. The article of claim 1, wherein said cover is form-fit to said applicator tip.

16. The article of claim 1, wherein said adhesive material is a synthetic or semi-synthetic polymerizable or cross-linkable monomer material.

17. The article of claim 16, wherein said applicator tip comprises a solid support having a polymerization or cross-linking initiator or rate modifier for said adhesive material disposed thereon or therein.

18. The article of claim 1, wherein said adhesive material has a viscosity of at least 60 cP at 25° C.

19. The article of claim 1, wherein said adhesive material comprises 1,1-disubstituted ethylene monomers.

20. The article of claim 1, wherein said adhesive material comprises α-cyanoacrylate monomers.

21. The article of claim 1, wherein the applicator tip is attached to the container body by a luer lock.

22. An article of manufacture for dispensing adhesive material, comprising:
    a container body,
    a hollow porous applicator tip having a proximal end that is attached to said container body, and a distal end located away from said container body, and
    an adhesive material located in said container body in a non-contacting relationship with said applicator tip prior to dispensing said adhesive material, wherein said adhesive material is a polymerizable or cross-linkable monomer material.

23. The article of claim 22, wherein a shape of said applicator tip is selected from the group consisting of dome, conical, cylindrical, chisel and polygonal shapes.

24. The article of claim 22, wherein said applicator tip is in a shape of a dome.

25. The article of claim 22, wherein said applicator tip is in a shape of a chisel.

26. The article of claim 22, wherein said applicator tip is in a shape of a cone.

27. The article of claim 22, wherein said adhesive material is a synthetic or semi-synthetic polymerizable or cross-linkable monomer material.

28. The article of claim 27, wherein said applicator tip comprises a solid support having a polymerization or cross-linking initiator or rate modifier for said adhesive material disposed thereon or therein.

29. The article of claim 22, wherein said adhesive material comprises 1,1-disubstituted ethylene monomers.

30. The article of claim 22, wherein said adhesive material comprises acyanoacrylate monomers.

31. The article of claim 22, wherein said adhesive material has a viscosity of at least 60 cP at 25° C.

32. The article of claim 22, wherein the applicator tip is attached to the container body by a luer lock.

33. A method of manufacturing the article of claim 1, comprising:
    attaching the applicator tip to the container body;
    dispensing a quantity of said polymerization or cross-linking accelerator or initiator for said synthetic or semi-synthetic material disposed thereon or therein, into said applicator tip;
    disposing said synthetic or semi-synthetic monomer material in said container body in a non-contacting relationship with said applicator tip; and
    sealing said container body.

34. The method according to claim 33, wherein said quantity of said polymerization or cross-linking accelerator or initiator is dispensed into said applicator tip from the proximal end of said applicator tip.

35. The method according to claim 33, wherein said sealing comprises attaching a cap to an open end of said container body.

* * * * *